US010248989B2

(12) United States Patent
Harkins et al.

(10) Patent No.: US 10,248,989 B2
(45) Date of Patent: Apr. 2, 2019

(54) DIGITAL ORDER TRACKING

(71) Applicant: CVS Pharmacy, Inc., Woonsocket, RI (US)

(72) Inventors: David Harkins, Providence, RI (US); Anna Lasko, Providence, RI (US); Kim Kiser, Tiverton, RI (US)

(73) Assignee: CVS Pharmacy, Inc., Woonsocket, RI (US)

(*) Notice: Subject to any disclaimer, the term of this patent is extended or adjusted under 35 U.S.C. 154(b) by 621 days.

(21) Appl. No.: 14/946,860

(22) Filed: Nov. 20, 2015

(65) Prior Publication Data

US 2017/0148086 A1    May 25, 2017

(51) Int. Cl.

| G16H 20/10 | (2018.01) |
|---|---|
| G06Q 30/06 | (2012.01) |
| H04L 29/08 | (2006.01) |
| H04L 29/06 | (2006.01) |
| G06Q 50/22 | (2018.01) |

(52) U.S. Cl.
CPC ......... *G06Q 30/0635* (2013.01); *G16H 20/10* (2018.01); *H04L 67/02* (2013.01); *H04L 67/42* (2013.01); *G06Q 50/22* (2013.01)

(58) Field of Classification Search
CPC . G06F 3/0482; G06F 17/30882; G16H 40/20; G16H 40/40; G16H 15/00; G16H 20/10
See application file for complete search history.

(56) References Cited

U.S. PATENT DOCUMENTS

| 8,386,926 B1* | 2/2013 | Matsuoka | G06F 17/273 715/256 |
|---|---|---|---|
| 2002/0049834 A1* | 4/2002 | Molnar | G06F 9/465 709/219 |
| 2003/0003931 A1* | 1/2003 | Silventoinen | H04L 51/063 455/466 |
| 2008/0015549 A1* | 1/2008 | Maughan | G06F 19/3456 604/890.1 |
| 2010/0241844 A1* | 9/2010 | Hussain | G06F 21/6218 713/150 |
| 2017/0091414 A1* | 3/2017 | Patel | G06F 19/3456 |
| 2017/0091416 A1* | 3/2017 | Mink | G06F 19/3456 |

OTHER PUBLICATIONS

Shirali-Shahreza, Mohammad, and M. Hassan Shirali-Shahreza. "Text steganography in SMS." Convergence Information Technology, 2007. International Conference on. IEEE, 2007. (Year: 2007).*
Shirali-Shahreza, Mohammad. "Steganography in MMS." Multitopic Conference, 2007. INMIC 2007. IEEE International. IEEE, 2007. (Year: 2007).*

* cited by examiner

*Primary Examiner* — Jonathan Durant
(74) *Attorney, Agent, or Firm* — Patent Law Works LLP

(57) ABSTRACT

An issue with a pharmacy order that requires user interaction to complete the order is detected. A status message that includes information tailored to the issue and a link to additional information is sent to the customer who placed the order. A request for the additional information is received via the link, and the additional information is transmitted for display on the client device.

18 Claims, 10 Drawing Sheets

300

400

500

Enhanced Order ready

502

600

602a — Out of Stock

DOT SMS Message:
CVS/Pharmacy: Theresa, your Rx for AMO is not in stock. Will text you when ready. Add'l info: m.cvs.com/1234567 or 888-888-8888. Reply HELP for help Expanded Verbiage (602b):
We do not have the medication available to fill your prescription.

We have placed an order, and will text you when your prescription is ready to be picked up in full.

If you are need of immediate medication, please call us to discuss options.

604a — Partial Fill

DOT SMS Message:
CVS/Pharmacy: Theresa, we can only provide a partial fill of your Rx for AMO. Add'l info: m.cvs.com/1234567 or 888-888-8888. Reply HELP for help Expanded Verbiage (604b):
We do not have enough supply on-hand to fill your entire prescription at this time.

We will provide you with some medication until we can complete your order in full. You will receive a text when the partial fill is ready.

If you have any questions or concerns, please call us. We are here to help.

606a — Med Not Covered

DOT SMS Message:
CVS/Pharmacy: Theresa, your Rx for AMO is not covered by insurance. Order Details: m.cvs.com/1234567 or call 888-888-8888. Reply HELP for help Expanded Verbiage (606b):
Your medication is not covered by your insurance at this time. You do have the option to pay for it out of pocket, or we can contact your doctor or an alternative.

If you receive an order ready text message, this means we have your Rx ready for pick up (if desired).

If not, we may be waiting to hear from you. Please call the pharmacy if you would like to discuss options.

FIG. 6

| | Need Updated Insurance (702a) | Refill Too Soon (704a) | Prior Authorization (706a) |
|---|---|---|---|
| DOT SMS Message | CVS/Pharmacy: Theresa, your Rx for AMO is being filled. Pls call 888-888-8888 with your insurance. RxDetails: m.cvs.com/1234567. Reply HELP for help | CVS/Pharmacy: Theresa, your Rx for AMO is too soon to fill. Will txt when ready. RxDetails: m.cvs.com/1234567 or 888-888-8888. Reply HELP for help | CVS/Pharmacy: Theresa, your Rx for AMO is pending insurance approval. See full Rx Status: m.cvs.com/1234567 or call 888-888-8888 Reply HELP for help |
| Expanded Verbiage | We are processing your prescription but are unable to bill the insurance on file.<br><br>Please call us with your updated insurance information. This will help prevent delay during the pickup process.<br><br>The pharmacy may process your prescription without your insurance while waiting for you to call back. | We were unable to fill your prescription today based on the last time this medication was filled.<br><br>If we are able to determine the next fill date, we will make every attempt to fill and text you when ready.<br><br>If you are in need of your medication and have not receive notification, please call the pharmacy to discuss. | Your insurance is requesting additional information from your doctor to determine if your Rx is covered by your insurance.<br><br>This process may cause a delay for you to receive your medication. You do have the option to pay for it (out of pocket or retail price).<br><br>The pharmacy cannot fill the Rx until we hear back from the doctor, insurance, or yourself.<br><br>If you would like us to fill the Rx for you at this time, please call the pharmacy. |

DIGITAL ORDER TRACKING

TECHNICAL FIELD

Embodiments of the present invention relate generally to pharmacy order status updates and, more particularly, to systems and methods for sending and receiving electronic messages relating to order status and order actions.

BACKGROUND

After a customer places an order at a pharmacy for a medication or other product, in many cases, no further contact with the customer is required or desired, and the customer returns at an appointed time to pick up his or her medication. In some cases, however, there is an issue with filling the order for the medication, and further contact with the customer is recommended or required—the customer's insurance information may be out of date, for example, or the time for pick-up may need to be adjusted. In some other cases, the customer may simply wish to check on the status of the order or remind him or herself of the pick-up time.

It may be difficult or inconvenient, however, for either the pharmacy or the customer to establish communication. The pharmacy may not have the customer's contact information available, or an available method of contact may not be one that the customer readily checks. The customer may not be familiar with available methods of contact the pharmacy or may not have time to look them up. These hurdles to communication may lead to frustration on the part of the customer at a lack of information, unnecessary return trips to the pharmacy on the part of the customer, or even medication that is never picked up by the customer. A need therefore exists for an improved method and system of pharmacy communication.

SUMMARY

Embodiments of the present invention include systems and methods for providing digital order status to customers of pharmacy orders of medication and other products. The status of the order is monitored automatically and/or manually, and if any event or issue occurs that requires customer action, such as detecting expired, missing, or incomplete insurance information, a status message is sent to the customer via, for example, simple-message-service ("SMS") text messaging, push notifications, or any other type of communication. The message may include text, which may be abbreviated to conform to the SMS service (to be less than, for example, 160 characters) and/or redacted to hide or obfuscate sensitive information, such as the customer's name or the name of the medication. The status message may further include a link, such as a hypertext-transfer protocol ("HTTP") link, that, when clicked, touched, or otherwise activated by the customer, accesses further information about the issue using, for example, a generic web browser, custom application, or other client program.

In one aspect, a system for providing status information of a pharmacy order includes a network interface configured for communication with a client device of a user; a non-volatile computer memory for storing information associated with the pharmacy order; and a computer processor configured for executing software instructions to: identify an issue with the pharmacy order that requires user interaction to complete the order; electronically transmit, to the client device of the user, a status message comprising information tailored to the issue and a link to additional information; electronically receive, from the client device of the user, a request for the additional information via the link; and electronically transmit, to the client device of the user, the additional information for display on the client device.

A confirmation message that the pharmacy order has been received may be electronically transmitted to the client device of the user. Identifying the issue may include detecting the issue at the system or receiving notification of the issue from a third party. The status message may be transmitted using simple-message-service text or a push notification. The link may be a hypertext-transfer-protocol link and the additional information may be transmitted using hypertext-transfer protocol. The issue may include a medication out of stock, a partial fill, medication not covered by insurance, updated insurance information needed, refill too soon, prior authorization, third attempt refill, or refill renewal denied. Sensitive information may be redacted from the status message and/or additional information. The additional information may include a login request.

In another aspect, a method for providing status information of a pharmacy order may include identifying, an issue with the pharmacy order that requires user interaction to complete the order; electronically transmitting, to the client device of the user, a status message comprising information tailored to the issue and a link to additional information; electronically receiving, from the client device of the user, a request for the additional information via the link; and electronically transmitting, to the client device of the user, the additional information for display on the client device.

A confirmation message that the pharmacy order has been received may be electronically transmitted to the client device of the user. Identifying the issue may include detecting the issue at the system or receiving notification of the issue from a third party. The status message may be transmitted using simple-message-service text or a push notification. The link may be a hypertext-transfer-protocol link and the additional information may be transmitted using hypertext-transfer protocol. The issue may include a medication out of stock, a partial fill, medication not covered by insurance, updated insurance information needed, refill too soon, prior authorization, third attempt refill, or refill renewal denied. Sensitive information may be redacted from the status message and/or additional information. The additional information may include a login request.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In the following description, various embodiments of the present invention are described with reference to the following drawings, in which:

FIGS. 6-8 illustrate exemplary redacted texts in accordance with embodiments of the present invention;

DETAILED DESCRIPTION

Figure 1:
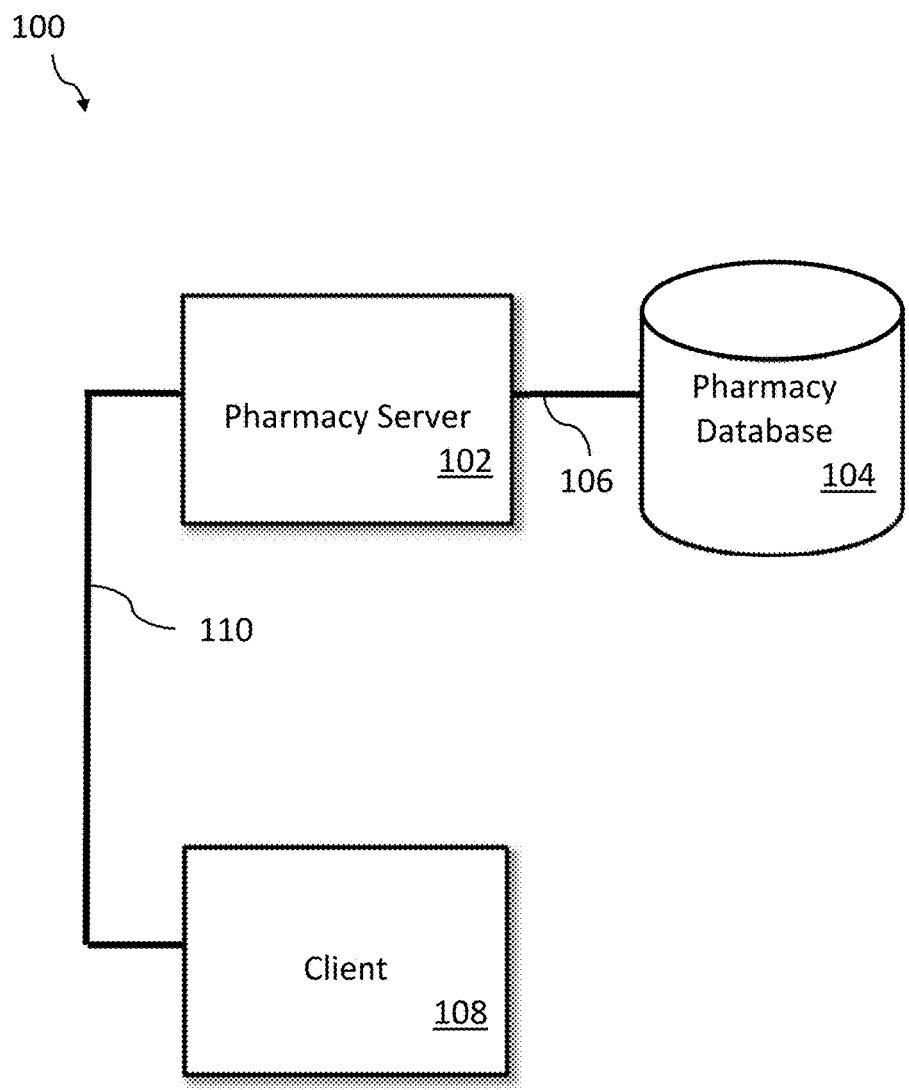
FIG. 1 illustrates a system for providing digital order status to pharmacy customers in accordance with an embodiment of the present invention.
Figure 2:
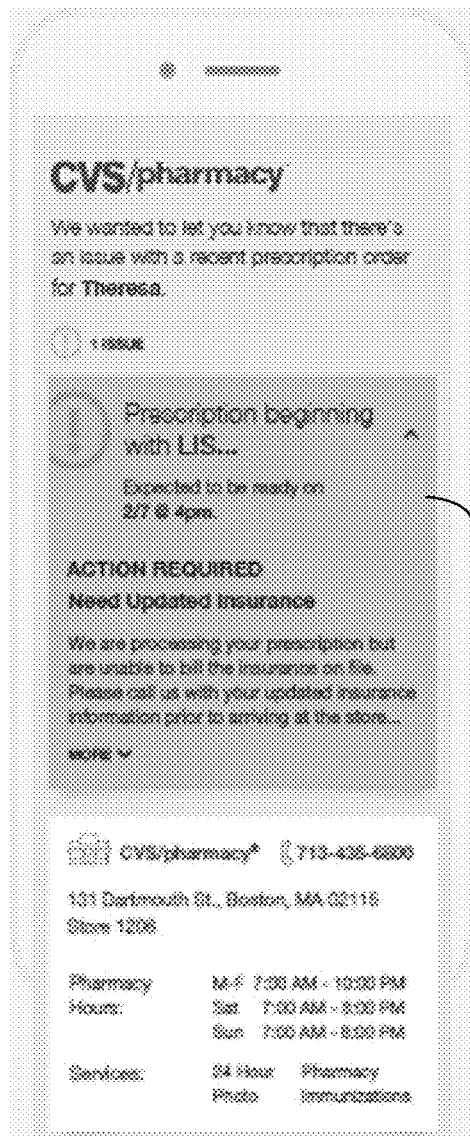
FIGS. 2-5 illustrate exemplary information views in accordance with embodiments of the present invention.
Figure 3:
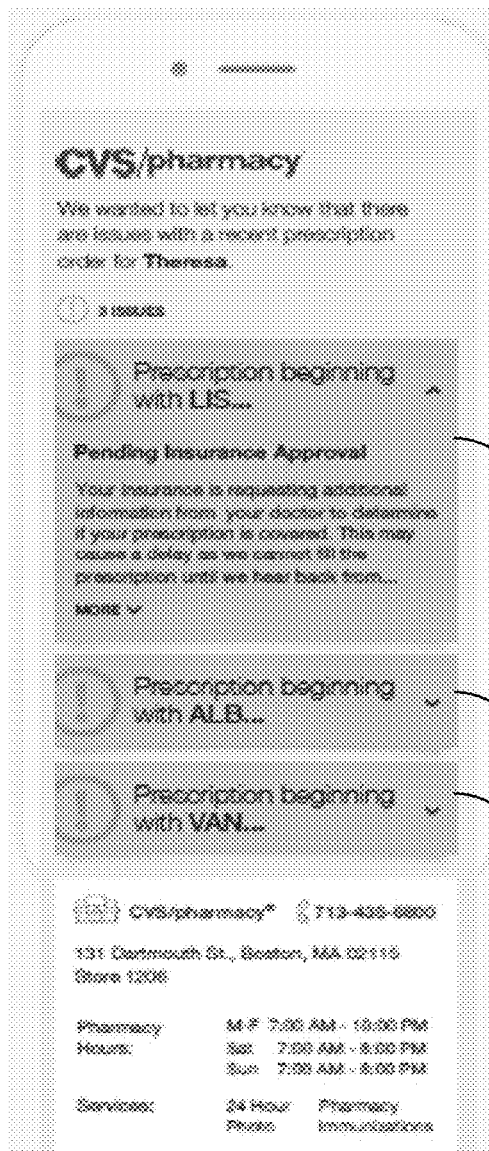
Figure 4:
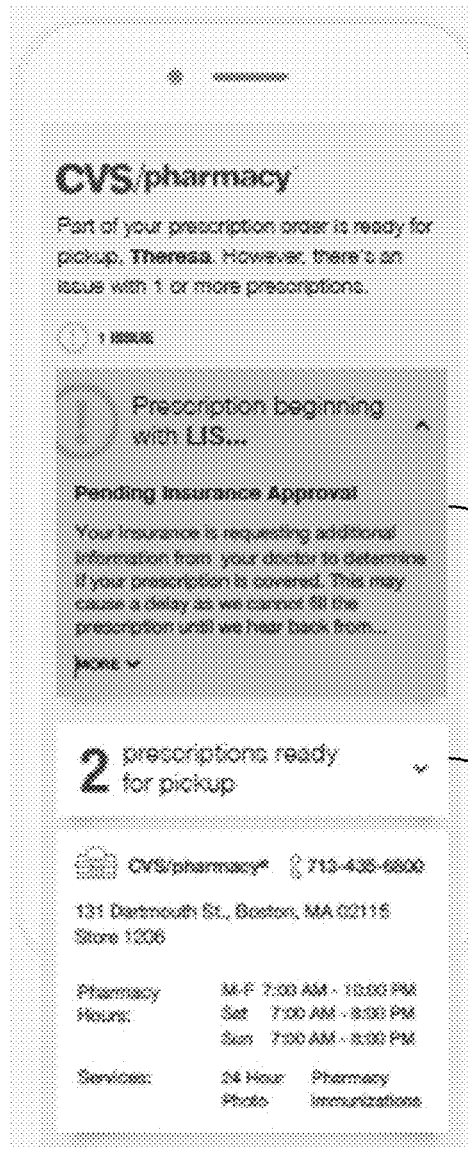
Figure 5:
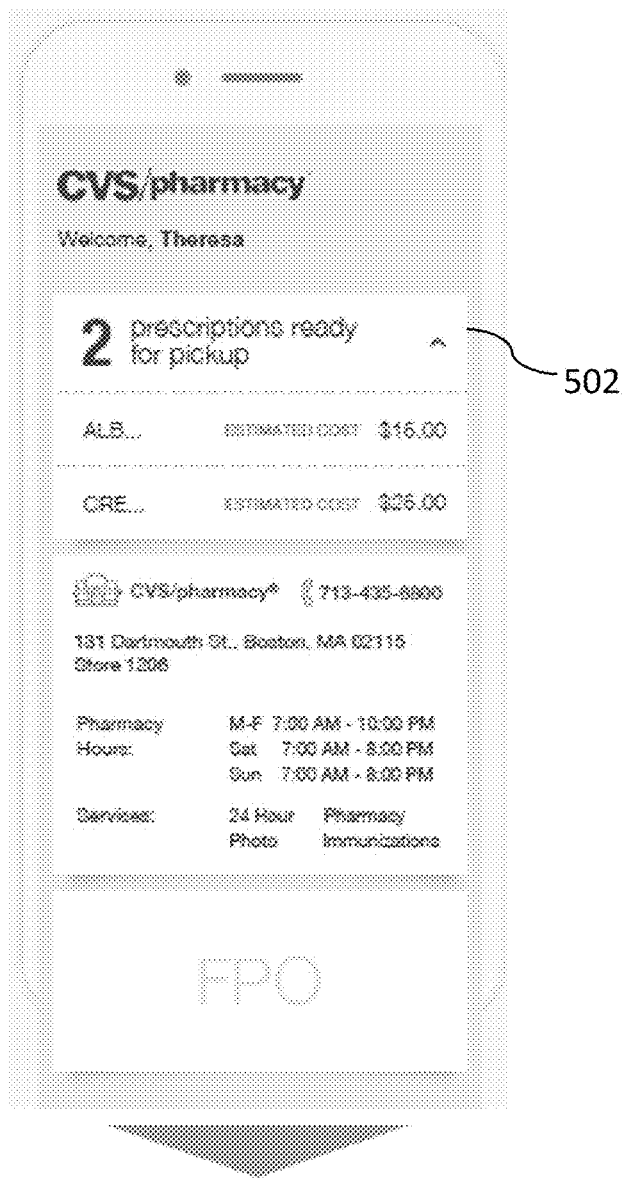

Various embodiments of the present invention include systems and methods for providing digital order status to customers of pharmacy orders of medication and other products. FIG. 1 is a block diagram of a computing environment 100 that includes a pharmacy server 102 and a pharmacy database 104 connected by a data connection 106. A client device 108, such as a cellular telephone, tablet computer, laptop computer, desktop computer, or any other type of client device, may communicate with the pharmacy server 102 via another data connection 110, which may be the same or a different network as the first data connection 106. In various embodiments, the data connection 110 is the Internet and/or a cellular network, such as a CDMA network. Any type of server, database, client, or network is within the scope of the present invention, however. Further details regarding the pharmacy server 102, pharmacy database 104, data connections 106, 110, and client 108 appear below in FIGS. 10 and 11 and associated text.

A pharmacy customer or person acting on behalf thereof, such as the customer's doctor, places an order at a pharmacy for medication or any other product. A clerk, technician, or other pharmacy worker may access a user account associated with the customer via the pharmacy server 102; the account information may be stored in the pharmacy database 104. The access may be achieved by entering, via a client device, information received from the customer or third party, such as the customer's name, date of birth, credit-card information, social-security number, prescription information, or any other type of identifying information. The entry may be performed manually using a keyboard, touchpad, or other data-entry device, automatically using a scanning device, such as a bar-code scanner, biometric sensor, near-field communication ("NFC") scanner, or any other type of scanning device, or (if the information is received electronically from a third party) entered automatically.

The user account may include any information associated with the customer, such as the customer's name, address, telephone number, email address, doctor name, medical insurance information, diagnosis history, prescription history, or any other such information. If the user account does not exist, the pharmacy worker may create it or prompt the customer to create it using a client device, such as the client device 108, other client device, or point-of-sale terminal. The user account creation may include prompting the customer for several pieces of information, such as his or her name, address, date of birth, telephone number, email address, insurance information, or any other information; in other embodiments, to facilitate creation of the account and encourage the customer to create the account, the information requested from the customer is the minimum required to later send electronic messages to the customer, such as only a phone number and/or email address.

Information regarding the customer's current pharmacy order may similarly be entered into the pharmacy server 102 and stored in the pharmacy database 104 or otherwise electronically associated with the customer and the user account belonging to the customer. If the pharmacy order is a new order, the customer or pharmacy worker may enter the information using a client device, such as a point-of-sale terminal, using a keyboard, touchscreen, scanning device, or other input device. If the pharmacy order is a refill or other type of order for which some or all information is already entered into the pharmacy database 104, the customer and/or pharmacy worker may only enter some information regarding the current pharmacy order; the some information may be, in some embodiments, a command to refill an existing prescription. The pharmacy order may come from the customer or a person acting on behalf of the customer, such as the customer's doctor.

Once the user account has been accessed and/or created and once the information regarding the pharmacy order is received, the pharmacy server 102 may transmit one or more messages to the client device 108 associated with the customer. In some embodiments, these messages are confirmation messages that confirm that one or more steps in the process of fulfilling the order are complete. The steps may include successful receipt of the pharmacy order, placement of the order into a fulfillment queue, fulfillment of the pharmacy order, or any other step; confirmation messages may be sent to the customer via the client device 108 after completion of one or more steps. In some cases, messages may be sent to the client device 102 at predetermined times whether a step has completed or not. For example, a message may be sent to the client device 102 every day at noon until an associated order is complete. In some embodiments, the customer adjusts the number, timing, and/or type of confirmation messages sent via a setting in his or her user account in the pharmacy database 104; the customer may also configure the type of confirmation message between, for example, SMS, push notifications, or email.

In some embodiments, the pharmacy server 108 sends one or more status messages to the client device 102 if an issue occurs regarding the pharmacy order and action on the part of the customer is required or desired. The issues may be detected automatically by comparing expected values to actual values, such as quantities of medication requested and in stock or may be detected manually. In other embodiments, information about the issues is received from one or more third parties electronically and/or manually, such as information from an insurer that a given medication is not covered by insurance. These issues may include but are not limited to a medication being out of stock, an insufficient quantity of a medication to fully fill an order, a medication not covered by the customer's insurance, out-of-date insurance information that requires updating, a refill request made too soon, a request by an insurance company for additional information from the customer and/or customer's doctor, lack of reply from the customer's doctor regarding a refill or other prescription after a certain number of attempts to contact the doctor (e.g., three attempts), lack of approval from the customer's doctor for a refill, and/or any other type of similar issue, including a general "catch-all" issue, such as unknown delay in filling the prescription. The status message may include text that indicates the type of issue and that requests that the customer take action thereon (such as selecting the included link described below). The status message may also include a telephone number that the customer may call to address the issue. The issues may be received and detected in real-time as they occur; the status messages may similarly be transmitted to the client device 102 in real time.

In some embodiments, sensitive information is redacted from the status message. If the status message is an SMS text message, the pharmacy server 102 cannot guarantee that the recipient of the SMS text message is indeed the customer. If the customer has provided a wrong number, lost his or her phone, or changed his or her phone number, a third party not associated with the customer may be able to read the SMS text message. In some embodiments, therefore, information is redacted from the status message such that the customer understands the message despite the redaction but it would be difficult or impossible for an unauthorized third party to glean sensitive information regarding the customer from the message. The sensitive information may include the customer's name, customer's address, customer's phone number (if different from the number to which the SMS text message was sent), medication name, medication quantity, number of refills remaining, pharmacy address, or any other such information.

In some embodiments, the message contains the redacted name of the customer in lieu of the full name of the customer. The customer name may be redacted to include only the first name of the customer, only the last name of the customer, or only a subset of characters from either or both of the first name and last name. For example, if the customer's name is "John Smith," the redacted name in the message may be "John," "Smith," "JS," "Jo Sm," or any other similar variation of the customer's full name.

In some embodiments, the message contains the redacted name of the medication in lieu of the full name of the medication. The medication name may be redacted to include only a subset of characters of the full name of the medication. For example, if the full name of the medication is "amoxicillin," the redacted name may be "AM," "AMO," "OXI," or any other subset. The subset may be the first one, two, three, or more characters of the full medication name or may be one, two, three, or more middle or end characters of the full medication name. If a customer has multiple medications in the same order and if those medications have similar names, more characters may be used to distinguish the medications. For example, if three characters are used, additional characters may be added (a fourth, fifth, or additional characters) until there is at least one unique character for each medication. If, however, a threshold number of characters is exceeded, such as five, six, or seven characters, or half the number of characters in the full medication name, no further characters are added even if the redacted names are the same or similar.

In some embodiments, other information may be included in the message in addition to or in lieu of the customer name and medication information. This other information may include all or part of the customer's address, date of birth, email address, pharmacy location, and/or any other information that the customer may read and use to identify the order as belonging to him or herself. Still other information may include an estimated pick-up time for the medication.

In some embodiments, abbreviations or other shortened language is used in the status message for ease of reading by the customer, to comply with technological limits (e.g., SMS texting's 160 character limit), or for any other reason. For example, "Rx" may be used in place of "prescription" and "add'l" may be used in place of "additional." In some embodiments, words are shortened only as necessary to comply with a technological limit, and if the limit is not close, the words are not shortened. If the limit is reached despite all practical abbreviations, the pharmacy server 102 may then send additional messages as required. If additional messages are sent (e.g., two SMS text messages instead of one), the abbreviations may be re-expanded.

In some embodiments, the status message further includes a link to additional information regarding the order and/or issue. The link may be, for example, an HTTP link, FTP link, or any other type of link. The link may include an address, such as an internet-protocol address, that identifies a computer server on a network such as the Internet; this portion of the link may be commonly used by a plurality of customers. Another portion of the link may be unique for the customer and/or order and include a unique sequence of letters, numbers, or other characters. The pharmacy server 102 may associate these characters with the customer and/or order and store them in the pharmacy database 104. The pharmacy server 102 may create the unique characters using a random generator, using a sequential counter, or by any other means. The characters may include a subset of characters that represent information about the customer or order, such as one, two, or more digits that represent a store number, country or state, date, or any other such information. Some or all of the link may instead or in additional be customizable for each customer; the customization may be requested or performed by the customer, pharmacy, or both. Customizations may include a unique but easy-to-remember sequence of characters, such as the customer's name, date of birth, or other such information, to enable the customer to more easily memorize the link and be able to enter it into a browser even if the customer does not have the originally sent link available.

If and when the customer selects the link by clicking, touching, or otherwise activating it on the client device 108, the client device 108 transmits a request to the pharmacy server 102. The request contains the unique characters in the link described above. When the pharmacy server 102 receives the request, it extracts the characters therefrom and searches the pharmacy database 104 for the customer or order associated therewith. For example, when the pharmacy server 102 created the link and characters within, it may have created a tuple in the pharmacy database 104 that uses the characters as a key. By accessing the pharmacy database 108 using the characters, the pharmacy server 102 identifies the customer and/or order.

After the customer selects the link, the pharmacy server 102 (and/or any other server) transmits additional information to the client device 102 for display thereon. In some embodiments, the client device 102 executes software instructions for a web browser, and the pharmacy server 102 transmits a web page for display thereon. In other embodiments, the client device 102 executes software instructions for a software application, such as a pharmacy application, that receives information and displays it on the screen of the client device 102. Any type of transmission protocol or display application is, however, within the scope of the present invention.

In some embodiments, the information is displayed on the client device 102 on a "landing page" that includes order information, order status, order issues, or any other such information. The landing page may be a web page or a screen displayed by a software application. Because the landing page may be displayed to a customer who has not authenticated him or herself to the pharmacy server 102, sensitive information in the landing page may be redacted as described above with reference to the status message. Thus, the landing page may display a redacted name of the customer and a redacted name of one or more medications. The landing page may further display one or more action items associated with one or more pharmacy orders and, in some embodiments, additional information for each action item. Any number of action items may be displayed. In some embodiments, the description of the action item may be expanded or collapsed. In some embodiments, the landing page displays pharmacy information (e.g., address, email address, and phone number) and/or an estimated time that the medication will be available for pickup.

FIGS. 2-5 illustrate exemplary landing pages 200, 300, 400, 500. Landing page 200 features a single expanded action item 202; landing page 300 features one expanded action item 302 and two collapsed action items 304, 306; landing page 400 features an expanded action item 402 and an order-ready indicator 404; and landing page 500 features an enhanced order-ready indicator 502. These landing pages 200, 300, 400, 500 are, however, exemplary, and any style, arrangement, color, of action items and order-ready indicators are within the scope of the present invention.

Figure 8:
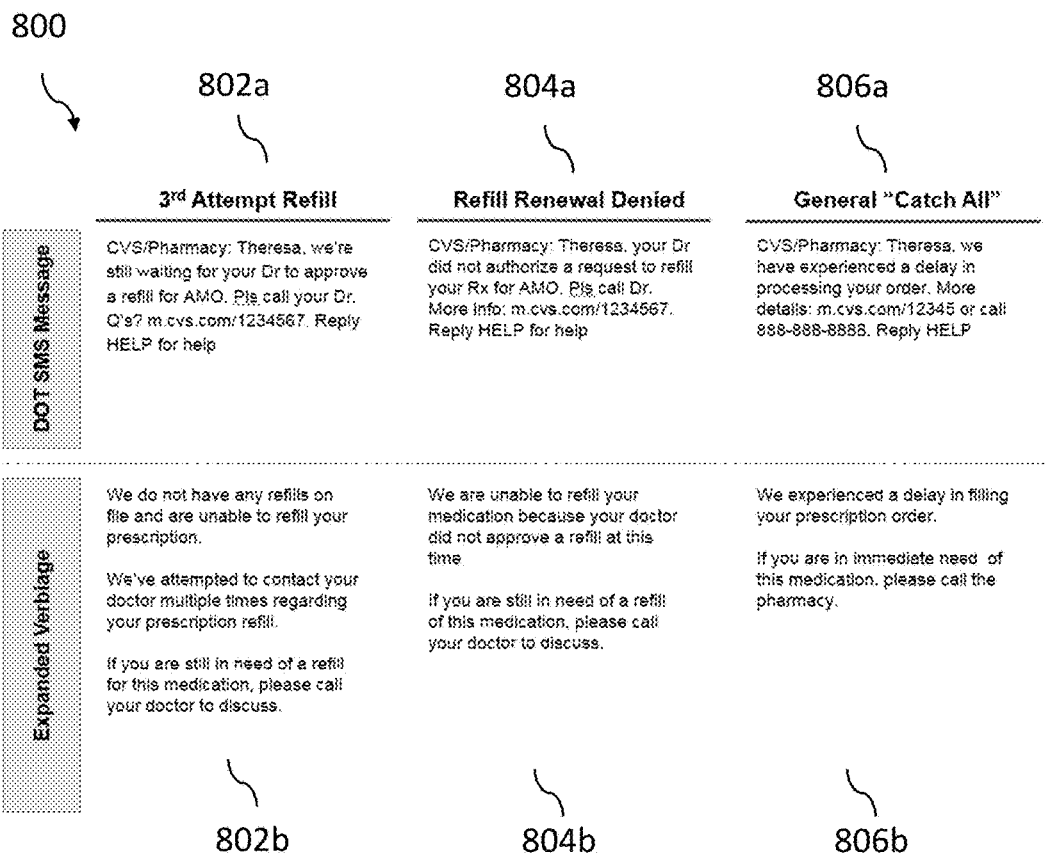

FIGS. 6-8 illustrate example text for status messages (i.e., the SMS messages sent to a client device 102) and corresponding example text for landing pages. In FIG. 6, status-message text 602a corresponds to landing-page text 602b for a medication being out of stock, status-message text 604a corresponds to landing-page text 604b for an insufficient quantity of a medication to fully fill an order, and status-message text 606a corresponds to landing-page text 606b for a medication not covered by the customer's insurance. In FIG. 7 status-message text 702a corresponds to landing-page text 702b for out-of-date insurance information that requires updating, status-message text 704a corresponds to landing-page text 704b for a refill request made too soon, and status-message text 706a corresponds to landing-page text 706b for a request by an insurance company for additional information from the customer and/or customer's doctor. In FIG. 8, status-message text 802a corresponds to landing-page text 802b for lack of reply from the customer's doctor regarding a refill or other prescription after a certain number of attempts to contact the doctor (e.g., three attempts), status-message text 804a corresponds to landing-page text 804b for lack of approval from the customer's doctor for a refill, and status-message text 806a corresponds to landing-page text 806b for a general "catch-all" issue. The present invention is not limit to only these messages, however.

Figure 9:
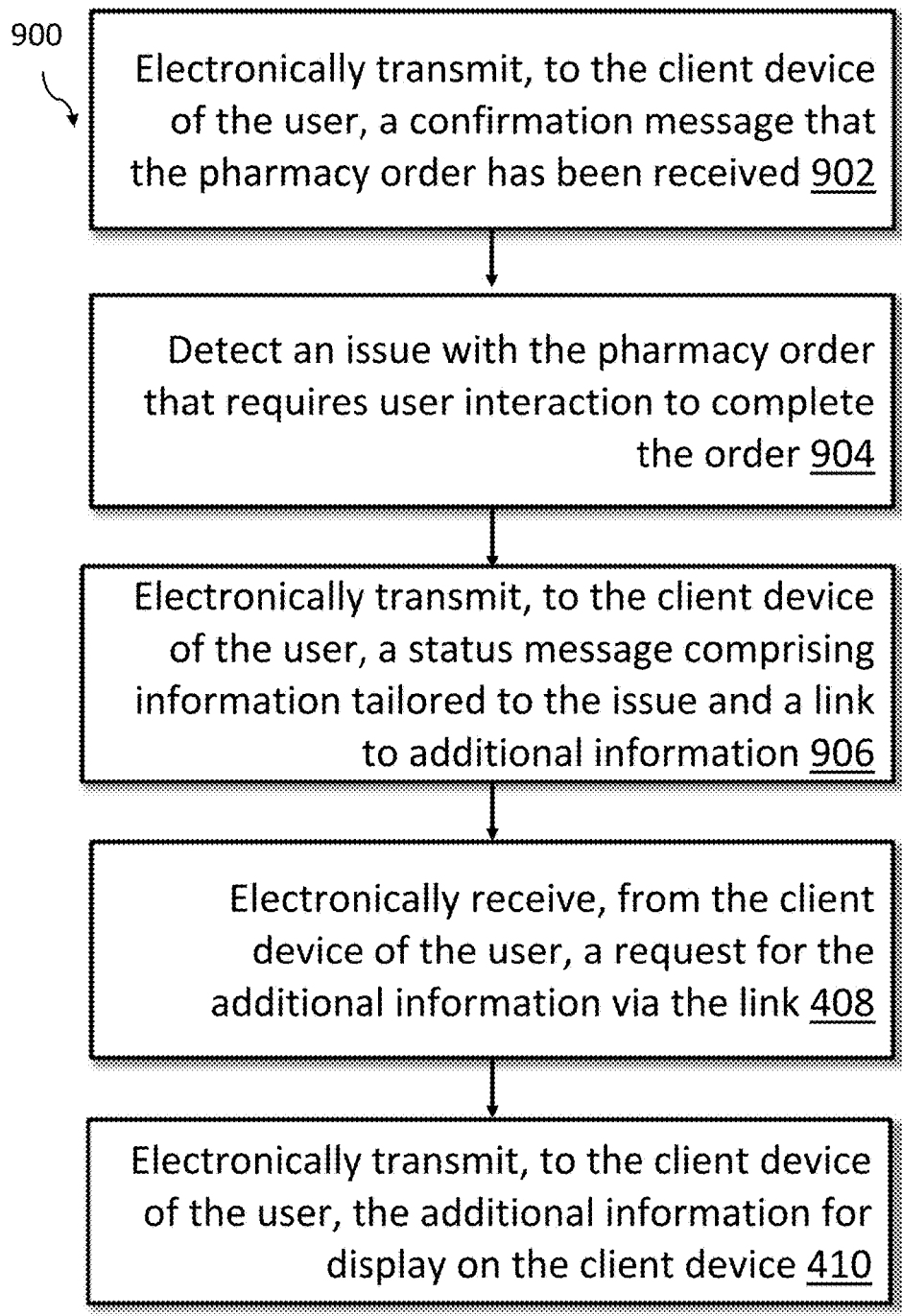
FIG. 9 illustrates a method for providing digital order status to pharmacy customers in accordance with an embodiment of the present invention.

FIG. 9 illustrates a method 900 in accordance with embodiments of the present invention. In a first step 902, a confirmation message that the pharmacy order has been received is electronically transmitted to the client device of the user. In a second step 904, an issue with the pharmacy order that requires user interaction to complete the order is detected. In a third step 906, a status message comprising information tailored to the issue and a link to additional information is electronically transmitted to the client device of the user. In a fourth step 908, a request for the additional information via the link is electronically received from the client device of the user. In a fifth step 910, the additional information for display on the client device is electronically transmitted to the client device of the user.

Figure 10:
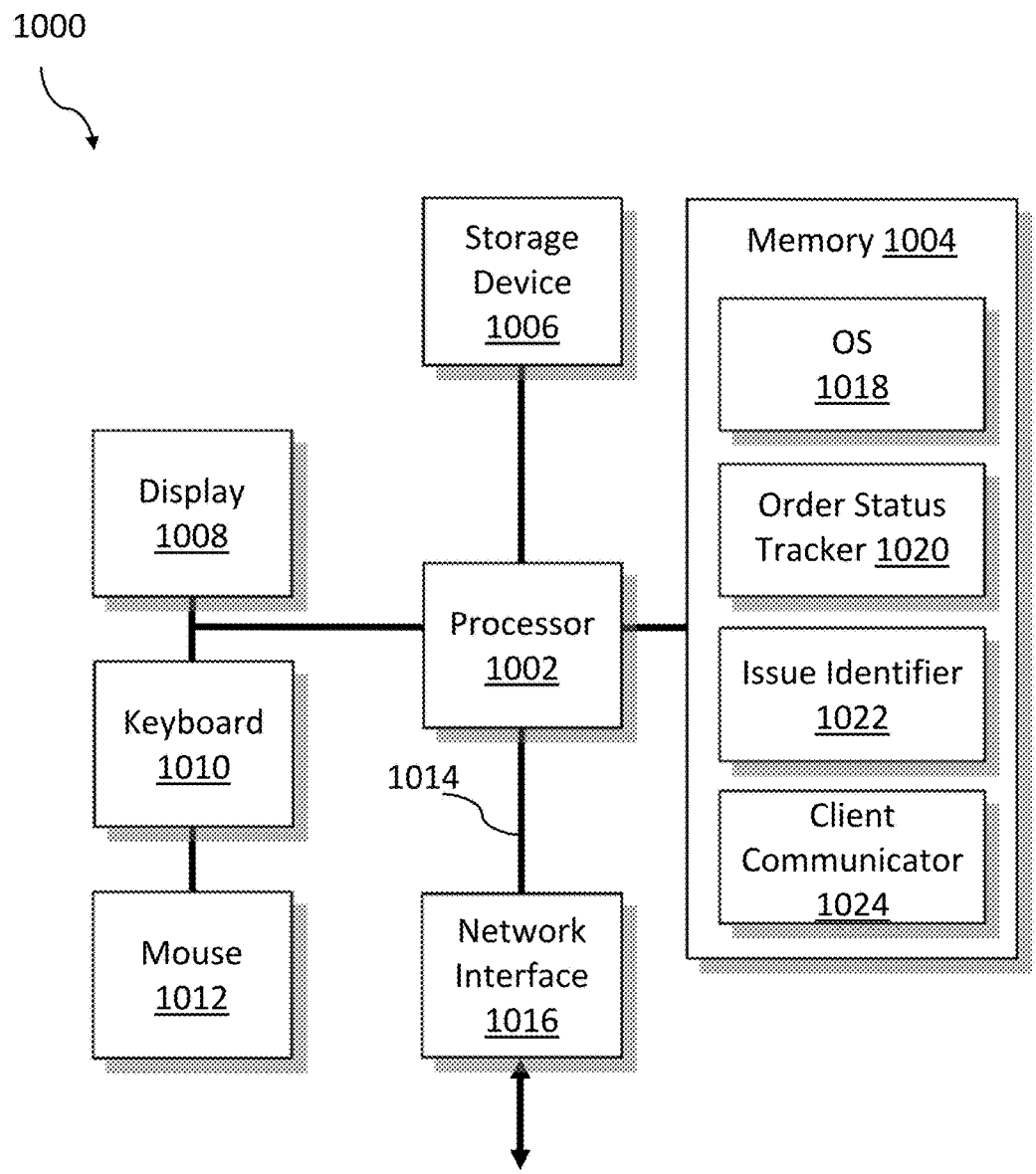
FIG. 10 illustrates an exemplary server computing device in accordance with an embodiment of the present invention.

FIG. 10 is a simplified block diagram of a suitably programmed general-purpose server 1000 implementing embodiments of the present invention; the server 1000 may be the pharmacy server 102. The server 1000 includes a processor 1002 having one or more central processing units (CPUs), volatile and/or non-volatile main memory 1004 (e.g., RAM, ROM, or flash memory), one or more mass storage devices 1006 (e.g., hard disks, or removable media such as CDs, DVDs, USB flash drives, etc., and associated media drivers, which may be used for the pharmacy database 104), a display device 1008 (e.g., a liquid-crystal display (LCD) monitor), user-input devices such as a keyboard 1010 and a mouse 1012, and one or more buses 1014 (e.g., a single system bus shared between all components, or separate memory and peripheral buses) that facilitate communication between these components. A network interface 1016 (e.g., a Wi-Fi or ETHERNET port) may be used to connect the computer 1000 to the Internet or other network.

The main memory 1004 may be used to store instructions to be executed by the processor 1002, conceptually illustrated as a group of modules. These modules generally include an operating system 1018 (e.g., a Microsoft WINDOWS, Linux, or APPLE OS X operating system) that directs the execution of low-level, basic system functions (such as memory allocation, file management, and the operation of mass storage devices), as well as higher-level software applications, such as an order status tracker 1020 for tracking customer orders, an issue identifier 1022 for identifying issues with an order, and a client communicator for sending and receiving messages to and from a client device. The various modules may be programmed in any suitable programming language, including, without limitation high-level languages such as C, C++, Java, Perl, Python, or Ruby or low-level assembly languages. The memory 1004 may further store input and/or output data associated with execution of the instructions as well as additional information used by the various software applications.

The server 1000 is described herein with reference to particular blocks, but this description is not intended to limit the invention to a particular physical arrangement of distinct component parts. The server 1000 is an illustrative example; variations and modifications are possible. The server 1000 may be implemented in a variety of form factors, including server systems, desktop systems, cloud-based computers, etc. A particular implementation may include other functionality not described herein, e.g., wired and/or wireless network interfaces, media playing and/or recording capability, etc. Further, the computer processor may be a general-purpose microprocessor, but depending on implementation can alternatively be, e.g., a microcontroller, peripheral integrated circuit element, a customer-specific integrated circuit ("CSIC"), an application-specific integrated circuit ("ASIC"), a logic circuit, a digital signal processor ("DSP"), a programmable logic device such as a field-programmable gate array ("FPGA"), a programmable logic device ("PLD"), a programmable logic array ("PLA"), smart chip, or other device or arrangement of devices.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for providing status information of a pharmacy order, the system comprising:
   a network interface configured for communication with a client device of a user;
   a non-volatile computer memory for storing information associated with the pharmacy order; and
   a computer processor configured for executing software instructions to:
      identify an issue with the pharmacy order that requires user interaction to complete the pharmacy order;
      generate a first status message using abbreviations, the first status message including information tailored to the issue;
      determine whether the first status message, including the abbreviations, exceeds a technological limit;
      responsive to determining that the first status message, including the abbreviations, exceeds the technological limit, re-expand the abbreviations of the first status message and generate a plurality of status messages, which include the information tailored to the issue, each of the plurality of status messages complying with the technological limit;
      electronically transmit, to the client device of the user, the plurality of status messages comprising information tailored to the issue and a link to additional information of the pharmacy order;
      electronically receive, from the client device of the user, a request for the additional information via the link; and
      electronically transmit, to the client device of the user, the additional information for display on the client device.

2. The system of claim 1, wherein the computer processor is further configured for executing software instructions to electronically transmit, to the client device of the user, a confirmation message that the pharmacy order has been received.

3. The system of claim 1, wherein identifying the issue comprises detecting the issue at the system or receiving a notification of the issue from a third party.

4. The system of claim 1, wherein the plurality of status messages is transmitted using a simple-message-service text or a push notification.

5. The system of claim 1, wherein the link is a hypertext-transfer-protocol link and the additional information is transmitted using a hypertext-transfer protocol.

6. The system of claim 1, wherein the issue comprises a medication out of stock, a partial fill, medication not covered by insurance, updated insurance information needed, refill too soon, prior authorization, third attempt refill, or refill renewal denied.

7. The system of claim 1, wherein the computer processor is further configured for executing software instructions to redact sensitive information from the plurality of status messages.

8. The system of claim 1, wherein the computer processor is further configured for executing software instructions to redact sensitive information from the additional information.

9. The system of claim 1, wherein the additional information comprises a login request.

10. A method for providing status information of a pharmacy order, the method comprising:
    identifying, an issue with the pharmacy order that requires user interaction to complete the pharmacy order;
    generating a first status message using abbreviations, the first status message including information tailored to the issue;
    determining whether the first status message, including the abbreviations, exceeds a technological limit;
    responsive to determining that the first status message, including the abbreviations, exceeds the technological limit, re-expanding the abbreviations of the first status message and generating a plurality of status messages, which include the information tailored to the issue, each of the plurality of status messages complying with the technological limit;
    electronically transmitting, to the client device of the user, the plurality of status messages comprising information tailored to the issue and a link to additional information of the pharmacy order;
    electronically receiving, from the client device of the user, a request for the additional information via the link; and
    electronically transmitting, to the client device of the user, the additional information for display on the client device.

11. The method of claim 10, further comprising electronically transmitting, to the client device of the user, a confirmation message that the pharmacy order has been received.

12. The method of claim 10, identifying the issue comprises detecting the issue using a computer processor or receiving a notification of the issue from a third party.

13. The method of claim 10, wherein the plurality of status messages is transmitted using a simple-message-service text or a push notification.

14. The method of claim 10, wherein the link is a hypertext-transfer-protocol link and the additional information is transmitted using a hypertext-transfer protocol.

15. The method of claim 10, wherein the issue comprises a medication out of stock, a partial fill, medication not covered by insurance, updated insurance information needed, refill too soon, prior authorization, third attempt refill, or refill renewal denied.

16. The method of claim 10, further comprising redacting sensitive information from the plurality of status messages.

17. The method of claim 10, further comprising redacting sensitive information from the additional information.

18. The method of claim 10, wherein the additional information comprises a login request.

* * * * *